United States Patent
Furuya

(12) 
(10) Patent No.: US 6,501,079 B1
(45) Date of Patent: Dec. 31, 2002

(54) ULTRAVIOLET-RAY IRRADIATION APPARATUS FOR STERILIZATION OF A LIQUID OR SLUDGY SUBSTANCE

(75) Inventor: Mitsumasa Furuya, Tokyo (JP)

(73) Assignee: Satoshi Ómura, Tokyo (JP)

( * ) Notice: Subject to any disclaimer, the term of this patent is extended or adjusted under 35 U.S.C. 154(b) by 0 days.

(21) Appl. No.: 09/391,041

(22) Filed: Sep. 16, 1999

(30) Foreign Application Priority Data

Feb. 25, 1999 (JP) .......................................... 11-048381

(51) Int. Cl.$^7$ ................................................ A61L 2/10
(52) U.S. Cl. ...................................... 250/437; 250/438
(58) Field of Search ................................. 250/437, 435, 250/438

(56) References Cited

U.S. PATENT DOCUMENTS 4,837,484 A * 6/1989 Eliasson et al. ............ 313/634
5,614,723 A * 3/1997 Oppenlander et al. ...... 250/437

FOREIGN PATENT DOCUMENTS

| JP | 60034784 A | 2/1985 |
| JP | 09237608 A | 9/1997 |
| JP | 10000228 A | 1/1998 |

* cited by examiner

*Primary Examiner*—Jack Berman
(74) *Attorney, Agent, or Firm*—Jacobson Holman PLLC

(57) ABSTRACT

An ultraviolet-ray irradiation apparatus for sterilization of a liquid or sludgy substance to be sterilized. The apparatus includes a double-wall ultraviolet-emission tube having an outer tube and a transparent, hollow inner tube permitting passage of ultraviolet rays. A static mixer is disposed within the hollow inner tube. A feeding unit causes the liquid or sludgy substance to be sterilized to pass through the inner tube. This structure enable uniform sterilization of the liquid or sludgy substance by ultraviolet rays.

2 Claims, 2 Drawing Sheets

ULTRAVIOLET-RAY IRRADIATION APPARATUS FOR STERILIZATION OF A LIQUID OR SLUDGY SUBSTANCE

BACKGROUND OF THE INVENTION

1. Field of the Invention

The present invention relates to an ultraviolet-ray irradiation apparatus for sterilization of a liquid or sludgy substance to be sterilized.

2. Description of the Related Art

Generally, ultraviolet rays are radiated onto a liquid or sludgy substance in order to sterilize the liquid or sludgy substance. However, since uniform irradiation is difficult to achieve, reliable sterilization is difficult.

SUMMARY OF THE INVENTION

An object of the present invention is to provide an ultraviolet-ray irradiator apparatus for sterilization which can uniformly and reliably radiate ultraviolet rays onto a liquid or sludgy substance in order to sterilize the substance in a safe and reliable manner.

In order to achieve the above object, the present invention provides an ultraviolet-ray irradiation apparatus for sterilization of a liquid or sludgy substance to be sterilized, comprising:

- a double-wall ultraviolet-emission tube having an outer tube and a transparent, hollow inner tube permitting passage of ultraviolet rays;
- a static mixer disposed within the inner tube;
- a feeding unit for causing a liquid or sludgy substance to be sterilized to pass through the inner tube; and
- an ultraviolet emission control unit for controlling emission of ultraviolet rays from the ultraviolet-emission tube.

According to the present invention, a double-wall ultraviolet-emission tube is employed, and a static mixer is disposed within a hollow inner tube located at the center of the ultraviolet-emission tube. A substance to be sterilized is caused to pass through the inner tube while being mixed by division, replacement, and superposition effects induced by the static mixer as well as being irradiated with ultraviolet rays through the entire outer circumferential surface of the inner tube. Therefore, ultraviolet rays can be radiated directly onto the substance to be sterilized in a close space, so that ultraviolet rays can be radiated onto the substance more uniformly as compared with a conventional scheme in which ultraviolet rays are radiated onto a substance through a thin separation wall.

In the ultraviolet-ray irradiation apparatus, an ultraviolet-ray-reflecting layer is preferably formed on an inner or outer surface of the outer tube of the double-wall ultraviolet-emission tube. In this case, ultraviolet rays can be efficiently radiated into the interior of the inner tube containing the static mixer.

The ultraviolet-ray irradiation apparatus preferably comprises temperature control means for maintaining the double-wall ultraviolet-emission tube at a predetermined temperature. In this case, the sterilization efficiency can be improved.

BRIEF DESCRIPTION OF THE DRAWINGS

Various other objects, features and many of the attendant advantages of the present invention will be readily appreciated as the same becomes better understood by reference to the following detailed description of the preferred embodiment when considered in connection with the accompanying drawings, in which.

DESCRIPTION OF PREFERRED EMBODIMENT

Figure 1:
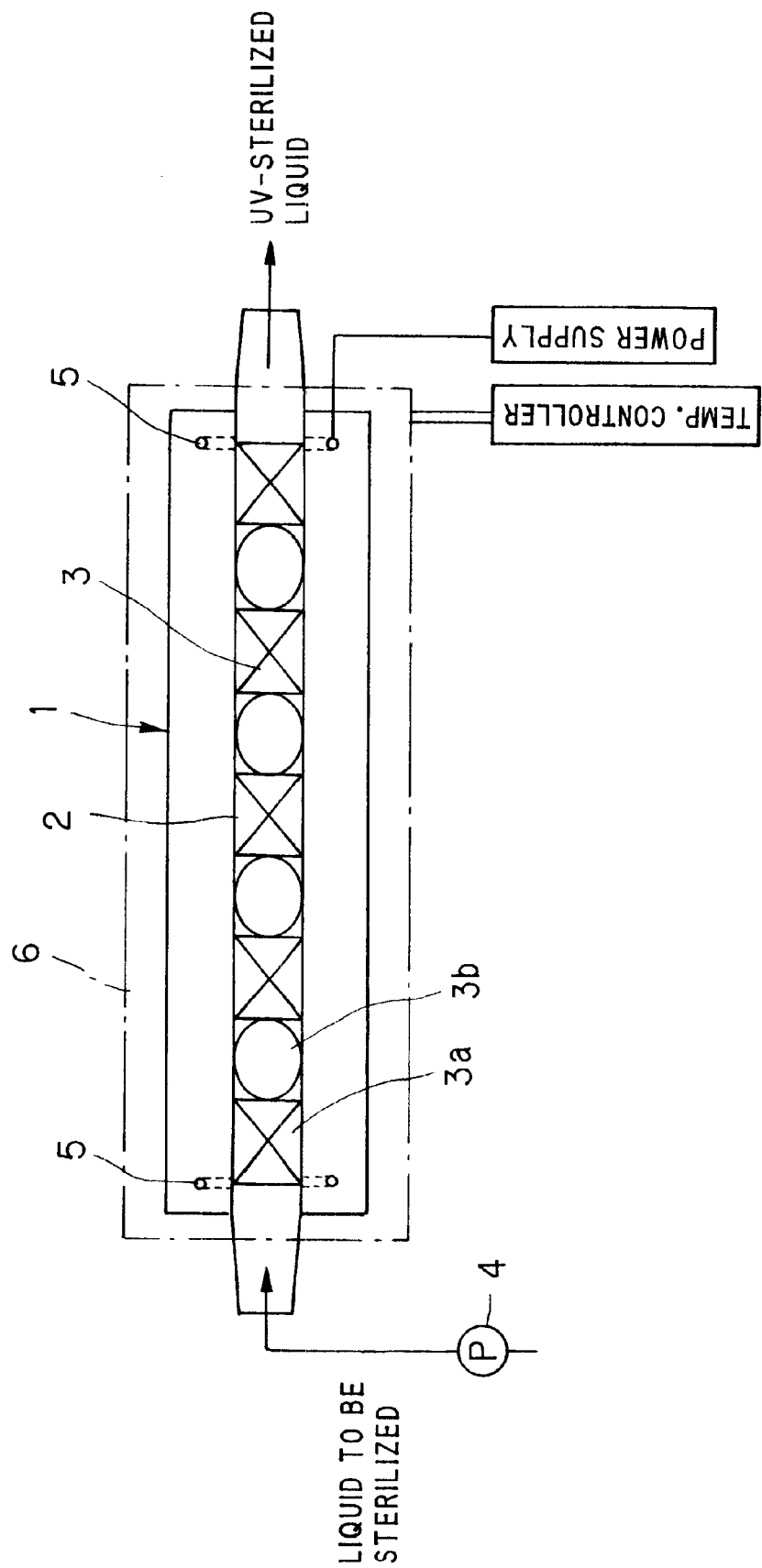
FIG. 1 is a longitudinal sectional view of an ultraviolet-ray irradiation apparatus for sterilization according to the present invention.
Figure 2:
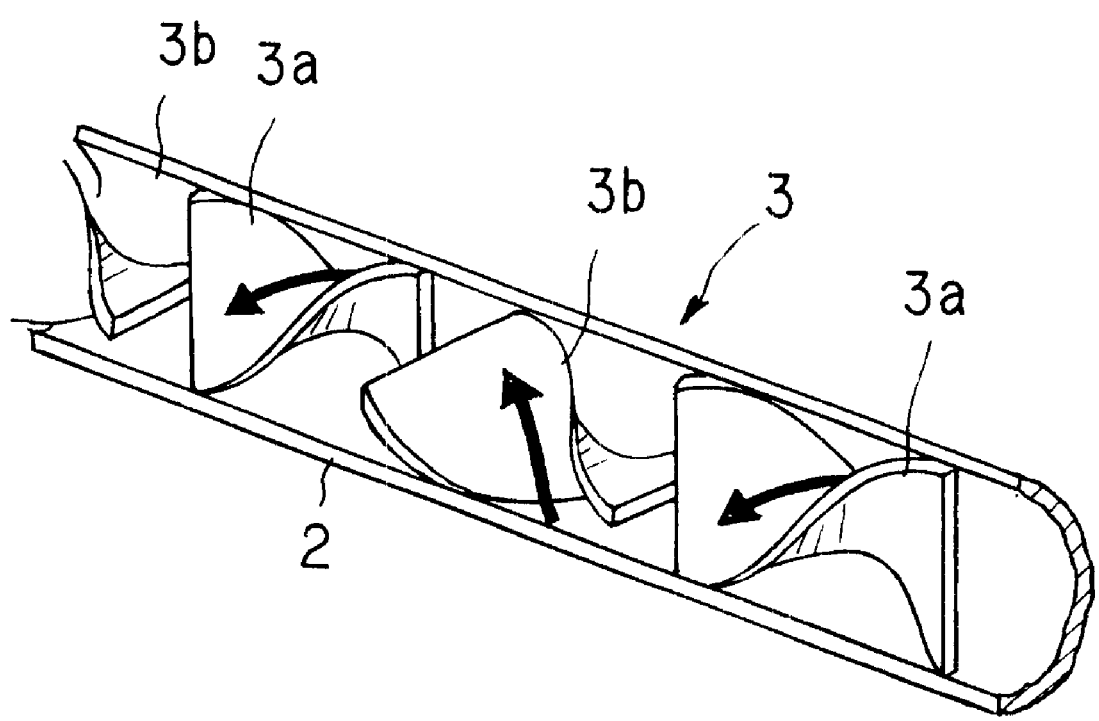
FIG. 2 is a schematic illustration showing the structure of a static mixer disposed within an inner tube of the ultraviolet-ray irradiation apparatus shown in FIG. 1.

As shown in FIG. 1, a double-wall ultraviolet-emission tube 1 has a hollow inner tube 2 at the center thereof. The inner tube 2 is transparent and therefore permits passage of ultraviolet rays. A static mixer 3 is disposed within the inner tube 2. As shown in FIG. 2, the static mixer 3 is composed of counterclockwise-twisted plate elements 3a and clockwise-twisted plate elements 3b. These plate elements 3a and 3b are inserted into and fixed to the inner tube 2 such that the plate elements 3a and 3b are alternately disposed and come into contact with each other at right angles. The total number of the plate elements 3a and 3b is determined in accordance with an intended application. A pump 4 is connected to the inner tube 2 in order to feed a liquid or sludgy substance to be sterilized into the inner tube 2. Thus, the substance to be sterilized passes through the inner tube 2, while undergoing division, replacement, and superposition effects induced by the plate elements 3a and 3b disposed in the inner tube 2.

A portion of the double-wall ultraviolet-emission tube 1 surrounding the inner tube 2 serves as an ultraviolet emitting section.

Specifically, electrodes 5 are disposed in the ultraviolet emitting section to be located at right and left ends of the ultraviolet-emission tube 1, and the ultraviolet emitting section is filled with ionized mercury vapor. Therefore, when an arc is generated between the electrodes 5, blue-green light containing a large dose of ultraviolet rays is emitted.

When the ultraviolet-emission tube 1 is turned on, ultraviolet rays are uniformly radiated into the interior of the inner tube 2 from the outer circumferential surface thereof. Therefore, ultraviolet rays can be radiated reliably and uniformly onto a liquid or sludgy substance to be sterilized that passes through the inner tube 2, in which the static mixer 3 is provided.

At this time, the liquid or sludgy substance passing through the inner tube 2 is mixed by the static mixer 3 through division, replacement, and superposition effects induced thereby. Therefore, uniform radiation of ultraviolet rays onto the substance to be sterilized can be performed in a uniform and reliable manner.

Further, an ultraviolet-ray-reflecting layer is preferably formed on an inner or outer surface of an outer tube of the double-wall ultraviolet-emission tube 1. In this case, all the emitted ultraviolet rays can be radiated into the interior of the inner tube 2 provided at the center of the ultraviolet-emission tube 1, so that the performance of radiating ultraviolet rays onto the substance to be sterilized can be enhanced.

The illumination intensity of the ultraviolet-emission tube 1 changes depending on the temperature of the tube 1. Therefore, an outer temperature control sleeve 6 enclosing the ultraviolet-emission tube 1 is preferably provided. Cooling water supplied from a temperature controller is passed through the outer temperature control sleeve 6 in order to maintain the ultraviolet-emission tube 1 at a temperature at which an optimal UV illumination intensity is obtained. Further, the voltage applied to the electrodes 5 is optimally controlled. In this way, control is performed to obtain an optimal UV illumination intensity. The degree of UV irradiation on a substance to be sterilized can be adjusted through an increase or decrease in the number of the elements 3a and 3b of the static mixer 3. Also, the degree of UV irradiation on a substance to be sterilized can be adjusted through adjustment of the feed rate of the substance.

According to the present invention, optimum UV irradiation can be performed through adjustment of the number of elements of the static mixer and/or through adjustment of the feeding rate of the substance to be sterilized. Therefore, treatment for inactivating viruses to be used in a vaccine and treatment of high-viscosity substances such as jam can be readily performed.

For example, an organic mercury compound (thimerosal) is used for inactivating treatment in a process for manufacturing a vaccine. However, when inactivating treatment is performed by use of the sterilizing apparatus according to the present invention, a danger caused by use of the organic mercury compound can be avoided. In addition, higher-level-biological-isolating process can be realized even in a high-level-fine-production process, and employment of an in-line scheme becomes easier.

Obviously, numerous modifications and variations of the present invention are possible in light of the above teachings. It is therefore to be understood that within the scope of the appended claims, the present invention may be practiced otherwise than as specifically described herein.

What is claimed is:

1. An ultraviolet-ray irradiation apparatus for sterilization of a liquid or sludgy substance to be sterilized, comprising:

a double-wall ultraviolet-emission tube having an outer tube and a transparent, hollow inner tube, the inner tube permitting passage of ultraviolet rays and passage therethrough of the substance to be sterilized;

a static mixer disposed within the inner tube for allowing uniform irradiation of the substance to be sterilized;

a feeding unit for causing the substance to be sterilized to pass through the inner tube;

an ultraviolet emission unit including electrodes for emitting ultraviolet rays, all of the electrodes being located between the inner tube and the outer tube so as to uniformly radiate the substance to be sterilized from an outer circumferential surface of the inner tube to an interior of the inner tube;

an ultraviolet-ray-reflecting layer formed on one of an inner and outer surface of the outer tube of the double-wall ultraviolet-emission tube for reflecting ultraviolet rays toward the substance to be sterilized in the inner tube; and temperature control means located outside of the outer tube for maintaining the double-wall ultraviolet-emission tube at a predetermined temperature.

2. The ultraviolet-ray irradiation apparatus according to claim 1, wherein the temperature control means includes a temperature control sleeve enclosing the double-wall ultraviolet-emission tube, and a temperature control unit for passing cooling water through the temperature control sleeve to maintain the double-wall ultraviolet-emission tube at a constant temperature.

* * * * *